United States Patent [19]

Sandler

[11] Patent Number: 5,319,136
[45] Date of Patent: Jun. 7, 1994

[54] PREPARATION OF PURE AMMONIUM THIOGLYCOLATE

[75] Inventor: Stanley R. Sandler, Springfield, Pa.

[73] Assignee: Elf Atochem North America, Inc., Philadelphia, Pa.

[21] Appl. No.: 120,253

[22] Filed: Sep. 10, 1993

[51] Int. Cl.$^5$ ............................................. C07C 53/00
[52] U.S. Cl. ..................................................... 562/512
[58] Field of Search ......................................... 562/512

[56] References Cited

U.S. PATENT DOCUMENTS

| | | | |
|---|---|---|---|
| 2,405,166 | 8/1946 | Reed et al. | 132/31 |
| 3,060,166 | 10/1962 | Dinsmore et al. | 562/512 |
| 3,331,743 | 7/1967 | Cook | 167/87.1 |
| 3,522,295 | 7/1970 | Konstantinov | 562/512 |
| 5,023,371 | 6/1991 | Tsui et al. | 562/512 |

FOREIGN PATENT DOCUMENTS 748858  5/1956  United Kingdom .

OTHER PUBLICATIONS

Austrian Patent No. 169,458 Leberl, Nov., 1951 (Chem. Abstr., vol. 46, 11597 c (1952).

Japanese 64–9918 Nozake et al., Jan. 1989 (Chem. Abstr., vol. 111, 102516a, 1993).

*Primary Examiner*—Arthur C. Prescott

[57] ABSTRACT

A process is disclosed for the preparation of pure ammonium thioglycolate from thioglycolic acid contaminated with the isopropyl ester of thioglycolic acid wherein the contaminated acid is reacted with aqueous ammonia or ammonium hydroxide at a pH of at least 6.5 to about 9.0 at elevated temperature.

14 Claims, No Drawings

PREPARATION OF PURE AMMONIUM THIOGLYCOLATE

BACKGROUND OF THE INVENTION

This invention relates to the preparation of a pure ammonium thioglycolate from thioglycolic acid contaminated with the isopropyl ester of thioglycolic acid. More particularly, it relates to the preparation of a low odor ammonium thioglycolate from thioglycolic acid contaminated with the very odoriferous isopropyl ester of thioglycolic acid by reaction of said acid with aqueous ammonia or ammonium hydroxide at a pH of at least 6.5 to about 9 and an elevated temperature.

THE PRIOR ART

Ammonium thioglycolic acid is a well known cosmetic agent used, for example, for hair softening and as a depilatory. Methods for deodorizing the thioglycolate which have been proposed include, for example, steam distillation under reduced pressure (Japanese Patent Publication No. 01/009918, Jan. 13, 1989), recrystallization (Austrian Patent No. 169,458, Nov. 26, 1951), and masking agent incorporation (U.S. Pat. No. 3,331,743, Jul. 18, 1967). Methods for producing ammonium thioglycolate from thioglycolic acid are known, for example, by reacting the acid with ammonium carbonate or bicarbonate, or ammonia (U.K. Patent Specification No. 748,858, Aug. 28, 1952).

SUMMARY OF THE INVENTION

This invention is a process for the preparation of pure ammonium thioglycolate from thioglycolic acid contaminated with the very odoriferous isopropyl ester of thioglycolic acid comprising reacting the contaminated thioglycolic acid with aqueous ammonia or ammonium hydroxide at a temperature within the range of 25° to 100° C. and at a pH of at least 6.5 to about 9, and continuing the reaction to obtain substantially complete conversion of said isopropyl ester to ammonium thioglycolate.

DETAILED DESCRIPTION OF THE INVENTION

Thioglycolic acid (TGA) contaminated with the isopropyl ester of thioglycolic acid (IPTG) is usually the result of the manufacture of thioglycolic acid, for example as discussed in U.S. Pat. No. 5,023,371 issued Jun. 11, 1991, where the acid is extracted from the reaction mixture with isopropyl ether. As little as 10 parts per million (ppm) of IPTG in TGA, or its salts, can produce an unpleasant odor (is odoriferous) which is unacceptable to cosmetic manufacturers and their customers. It is desirable that substantially complete removal (down to 8 ppm and below) is accomplished in the preparation of the ammonium thioglycolate (ATG) from TGA. The contaminated TGA used in the process of this invention has an odoriferous amount of IPTG present therein which ranges from above 8 or 10 ppm and higher. Generally, the IPTG content will be from above 8 to about 200 ppm. Additionally, if one desires to use the process to remove small (nonodoriferous) amounts, below 8 ppm, from the ATG, this process also has utility and such practice is intended to be covered by the appended claims.

In the neutralization of TGA with dry ammonia (water free), cleavage of the isopropyl ester (IPTG contaminate) to form ATG cannot occur. It is necessary that aqueous ammonia or ammonium hydroxide be used for neutralization to both convert the TGA to ATG and the IPTG to ATG. The original concentration of the aqueous ammonia or ammonium hydroxide used for this invention, but prior to TGA addition, broadly ranges from about 10 to about 50% by weight, preferably from about 20 to about 40%. Equations demonstrating these reactions are as follows:

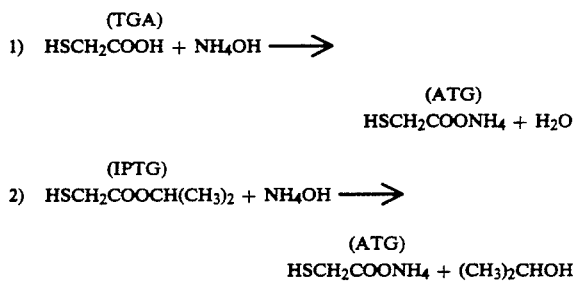

1) $\text{HSCH}_2\text{COOH} + \text{NH}_4\text{OH} \longrightarrow$ (TGA)

$\text{HSCH}_2\text{COONH}_4 + \text{H}_2\text{O}$ (ATG)

2) $\text{HSCH}_2\text{COOCH}(\text{CH}_3)_2 + \text{NH}_4\text{OH} \longrightarrow$ (IPTG)

$\text{HSCH}_2\text{COONH}_4 + (\text{CH}_3)_2\text{CHOH}$ (ATG)

The results of the titration of TGA with varying amounts of aqueous ammonia to vary the pH, demonstrated that the equivalence point (point where 1 equivalent of TGA reacts with 1 equivalent of aqueous ammonia) occurs at a pH of 6.11–6.12 on the titration curve. However, it has been found that unless the pH of the neutralization reaction is at least 6.5, preferably at least 7.5, the conversion of the IPTG contaminant to ATG is incomplete. Thus, the pH range of the process is from at least 6.5 to about 9.0, preferably from at least 7.5 to about 8.5. The upper end of the range is established by the fact that higher pH values serve no useful purpose in this process and that end users require a product which has a lower pH for cosmetic use. The lower end of the pH range is critical because of the failure of the reaction at lower acidity to provide substantially complete conversion of the odoriferous IPTG to ATG. The pH may be adjusted by manipulation of the mole ratio of reactants used or by the addition of another neutralizing agent, although manipulation of the mole ratio is preferred. The mole ratio of the reactants (TGA-NH$_3$) should range from 1.0:1.01 to 1.0:1.2, preferably 1.0:1.01 to 1.0:1.05. If the pH at, for example, a mole ratio of 1.0:1.0 is too low, another neutralizing agent may be incorporated into the aqueous reaction mix to bring the pH within the prescribed range. For example, ammonium carbonate, ammonium bicarbonate or dry ammonia, and the like may be used for this purpose.

The temperature of the neutralization reaction broadly ranges between 25° and 100° C., preferably between about 60° and about 80° C. It is advantageous to allow the exothermic reaction to proceed without cooling thereby producing a reaction temperature of 75°–80° C.

The reaction time is sufficient to reduce the IPTG content in the ATG to a point where the odor is no longer objectionable or, if no odor is originally detectable, to the point where there is a reduction of the IPTG content. Generally, about 0.5 to about 3 hours, but preferably about 0.5 to about 1.5 hours is spent for the reaction. The IPTG content in the ATG product should be no greater than about 8 ppm, preferably less than 2 ppm, and most preferably zero ppm.

It is advantageous, from the standpoint of a commercially preferred product, to vacuum strip the ATG product of this reaction to remove low boiling components, e.g., isopropyl alcohol. This is accomplished at a reduced pressure ranging from about 10 to about 50 mm. Hg, preferably no higher than about 30 mm. Hg (torrs) and a temperature of 25° to about 40° C., preferably about 30° C.

On completing the neutralization reaction, before or after the optional stripping procedure, the product pH may be adjusted to meet cosmetic formulator's specifications. The pH of the final product will generally range from about 5 to about 6.5, preferably from 5 to 6. This pH adjustment may be accomplished, for example, by the addition of an acidic liquid such as a solution of a mineral acid or innocuous organic acid, for example, hydrochloric acid.

The following examples are set forth to demonstrate the process of this invention.

EXAMPLE 1

To 30.7 g of TGA with an IPTG content of 50 ppm, was added dropwise without cooling 22.1 g of $NH_4OH$ (29.8% $NH_3$) to give a pH of 6.5. A gas chromatogram of this sample by headspace gas chromatography (GC) with a flame ionization detector showed a small amount (estimated 1–2ppm) of IPTG.

The addition of 0.625 g of ammonium hydroxide to the sample gave a pH of 8.0 and another headspace GC analysis with a flame ionization detector indicated no residual IPTG.

EXAMPLE 2

To 1304.1 g of the IPTG contaminated TGA of Example 1, was added dropwise 1023.5 ml of ammonium hydroxide (28.9% as $NH_3$) without cooling to give a final product with a pH of 6.95 (the reaction temperature reached 75°–80° C. during the addition of the ammonium hydroxide). The reaction mixture was stored for 1–2 hours until the reaction mixture cooled to room temperature. A composite of 4 batches made similarly was prepared and a GC headspace analysis with a flame photometric detector indicated a small peak eluting where IPTG occurs. Adding 12.0 ml. of ammonium hydroxide to the composite batch of 8013.9 g and storing for 1 hour gave a pH reading of 7.27. A GC headspace analysis with a flame photometric detector was again run and indicated no trace of IPTG.

The latter sample was subjected to vacuum stripping on a rotoevaporator at 30° C. for 10 minutes at 15 mm Hg pressure to remove low boiling components.

I claim:

1. A process for preparing pure ammonium thioglycolate from thioglycolic acid contaminated with the isopropyl ester of thioglycolic acid comprising reacting the contaminated thioglycolic acid with sufficient aqueous ammonia or ammonium hydroxide to raise the pH of the reaction to within the range of at least 6.5 to about 9.0 and at a temperature ranging from about 25° to 100° C., and continuing the reaction to obtain substantially complete conversion of said isopropyl ester to ammonium thioglycolate.

2. The process of claim 1 wherein the thioglycolic acid is contaminated with an odoriferous amount of isopropyl ester of thioglycolic acid.

3. The process of claim 2 wherein the temperature of the reaction is its exothermic temperature.

4. The process of claim 2 wherein the original concentration of the aqueous ammonia or ammonium hydroxide has a concentration of about 10 to 50% by weight.

5. The process of claim 2 wherein the temperature of the reaction ranges between about 60° and about 80° C.

6. The process of claim 2 wherein the contaminated thioglycolic acid is reacted with the aqueous ammonia or ammonium hydroxide at a mole ratio (thioglycolic acid-ammonia) within the range of 1.0:1.01 to 1.0:1.2.

7. The process of claim 2 wherein the reaction time extends from 0.5 to 3 hours.

8. A process for producing low odor ammonium thioglycolate from thioglycolic acid contaminated with more than 8 to about 220 ppm of isopropyl ester of thioglycolic acid comprising reacting the contaminated thioglycolic acid with aqueous ammonia or ammonium hydroxide at a mole ratio (thioglycolic acid-ammonia) within the range of 1.0:1.01 to 1.0:1.2, a pH within the range of at least 6.5 and 9.0, a temperature ranging from about 60° to about 80° C. and for a time extending from about 0.5 to about 1.5 hours.

9. The process of claim 8 wherein the original concentration of the aqueous ammonia or ammonium hydroxide ranges from about 20 to about 40% by weight.

10. The process of claim 8 wherein the pH of the reaction is within the range of about 7.5 and about 8.5.

11. The process of claim 8 wherein the ammonium thioglycolate product is vacuum stripped to remove low boiling components.

12. The process of claim 11 wherein the product is vacuum stripped at a reduced pressure in the range of about 10 to about 50 mm. Hg and a temperature within the range of 25° to about 40° C.

13. The process of claim 11 wherein the pH of the ammonium thioglycolate product is adjusted downward to between about 5 and about 6.

14. The process of claim 12 wherein the pH of the ammonium thioglycolate product is adjusted downward to between about 5 and about 6.

* * * * *